United States Patent [19]

Lindsey

[11] 4,084,587
[45] Apr. 18, 1978

[54] FLUID HEATING APPARATUS

[75] Inventor: Joseph W. Lindsey, Salt Lake City, Utah

[73] Assignee: Arbrook, Inc., Arlington, Tex.

[21] Appl. No.: 596,789

[22] Filed: Jul. 17, 1975

[51] Int. Cl.² .......................................... A61M 16/00
[52] U.S. Cl. .................................. 128/193; 219/305; 219/275; 261/DIG. 65; 165/169; 239/338
[58] Field of Search ............... 219/296, 299, 301, 303, 219/304, 305, 306, 544, 531, 271, 273, 275; 239/338; 128/192, 193, 194, 212; 261/DIG. 65, 142; 165/169, 170

[56] References Cited

U.S. PATENT DOCUMENTS

| 803,795 | 11/1905 | Stevens | 338/278 |
|---|---|---|---|
| 942,874 | 12/1909 | Stevens | 219/305 |
| 1,554,219 | 9/1925 | Kitchen | 128/193 |
| 2,040,630 | 5/1936 | Silten | 128/193 |
| 3,096,426 | 7/1963 | Axelson | 219/305 |
| 3,458,948 | 8/1969 | Curtis et al. | 219/275 |
| 3,718,805 | 2/1973 | Posey | 219/305 |
| 3,820,540 | 6/1974 | Hirtz et al. | 128/192 |
| 3,864,544 | 2/1975 | Amerongen | 128/193 |

Primary Examiner—Robert W. Michell
Assistant Examiner—Henry J. Recla

[57] ABSTRACT

A fluid heating apparatus for use in medical applications in the heating of water for use in a nebulizer is provided having a heated passageway for connecting between a water reservoir and a nebulizer head for heating only the water being used immediately before use. The passageway may be formed at the interfacing surfaces of a housing and an insert. The insert may be coated with a biocompatible material which possesses certain heat conductive properties while providing a water seal. A channel may transverse the surface of the coating to establish the passageway. An electrical heater may be located within the insert.

1 Claim, 17 Drawing Figures

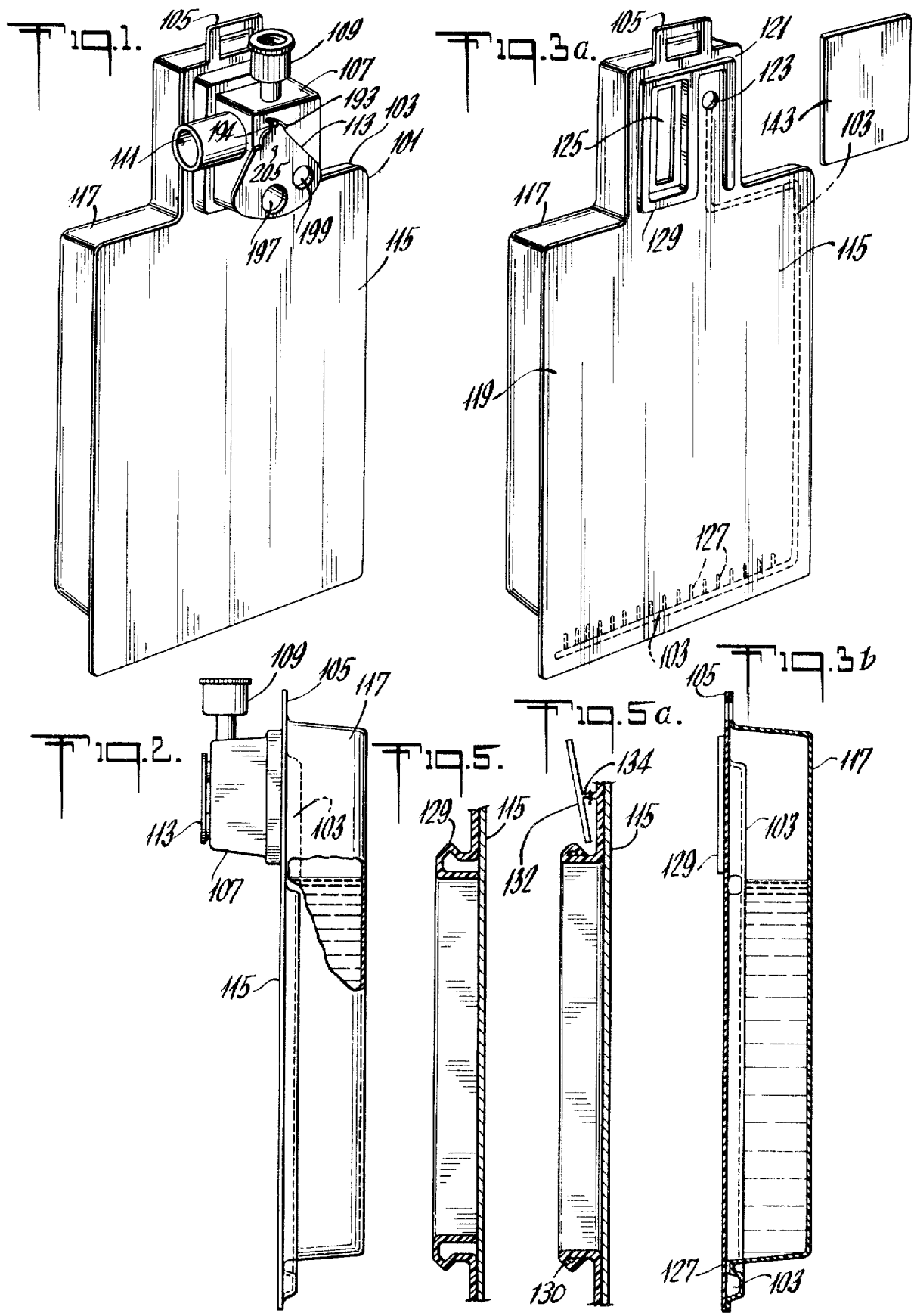

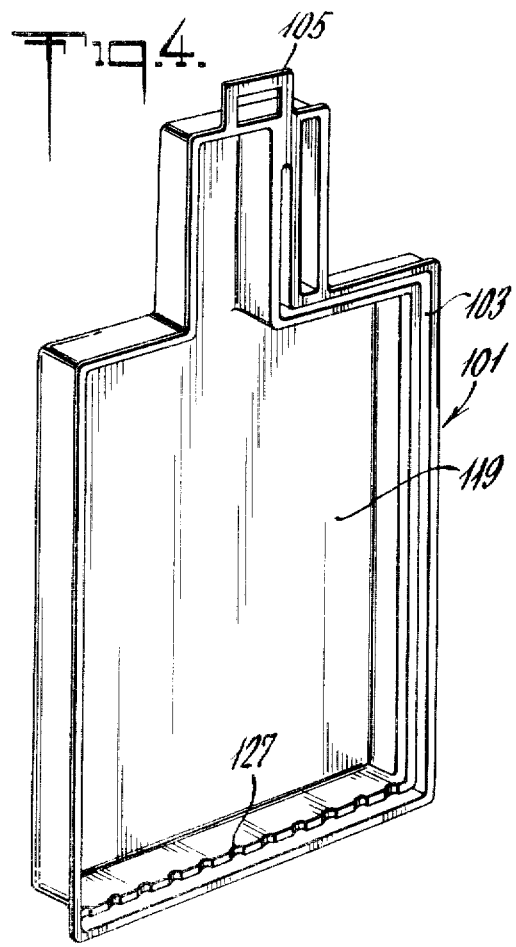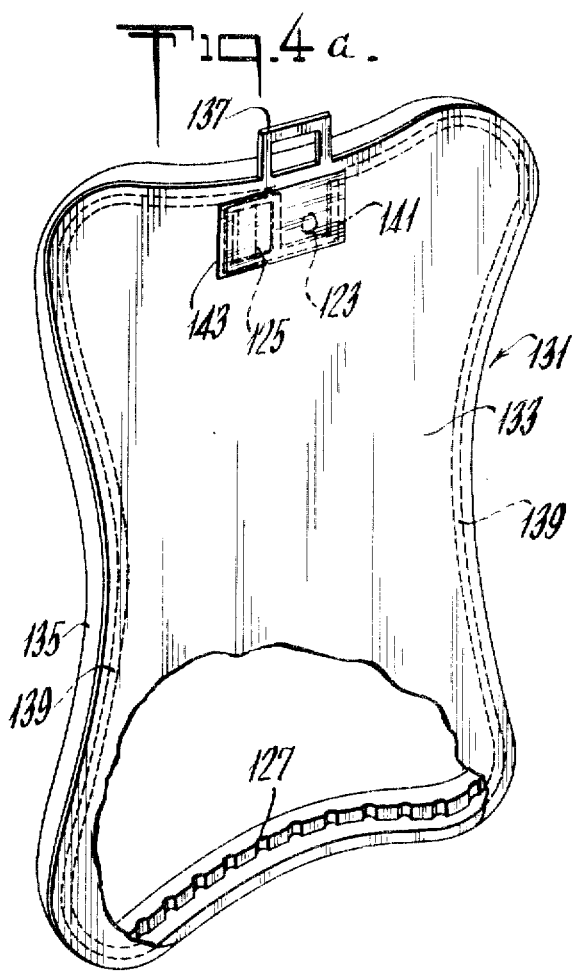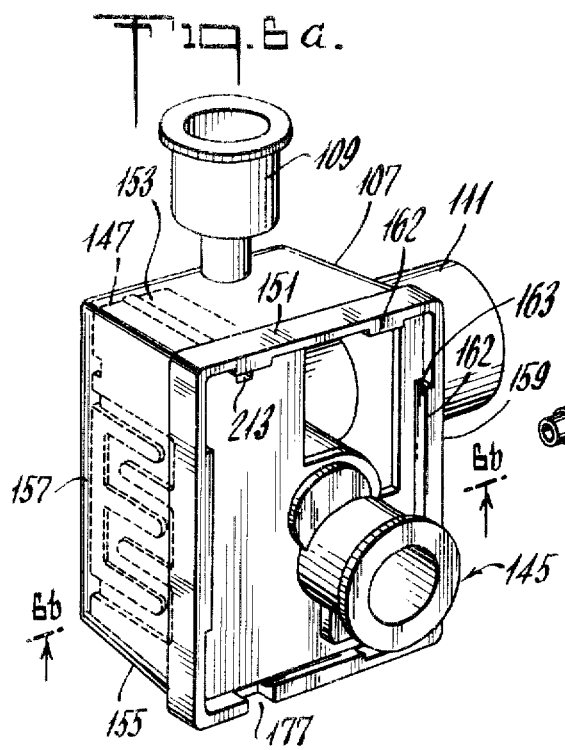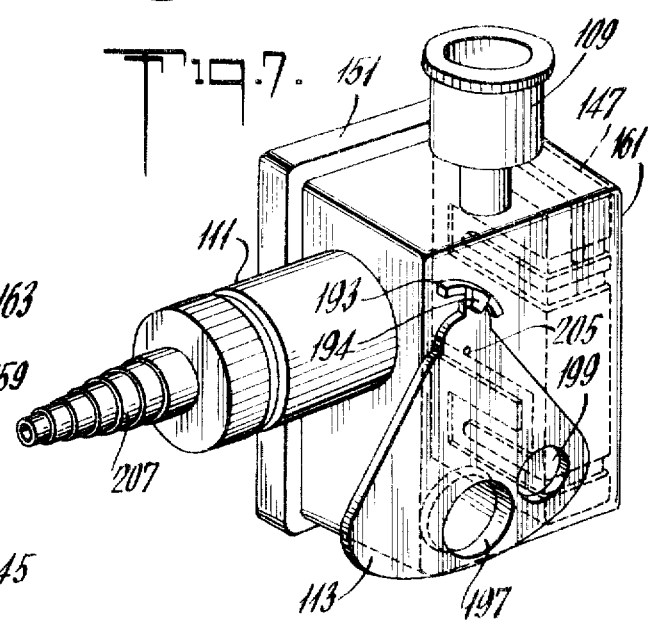

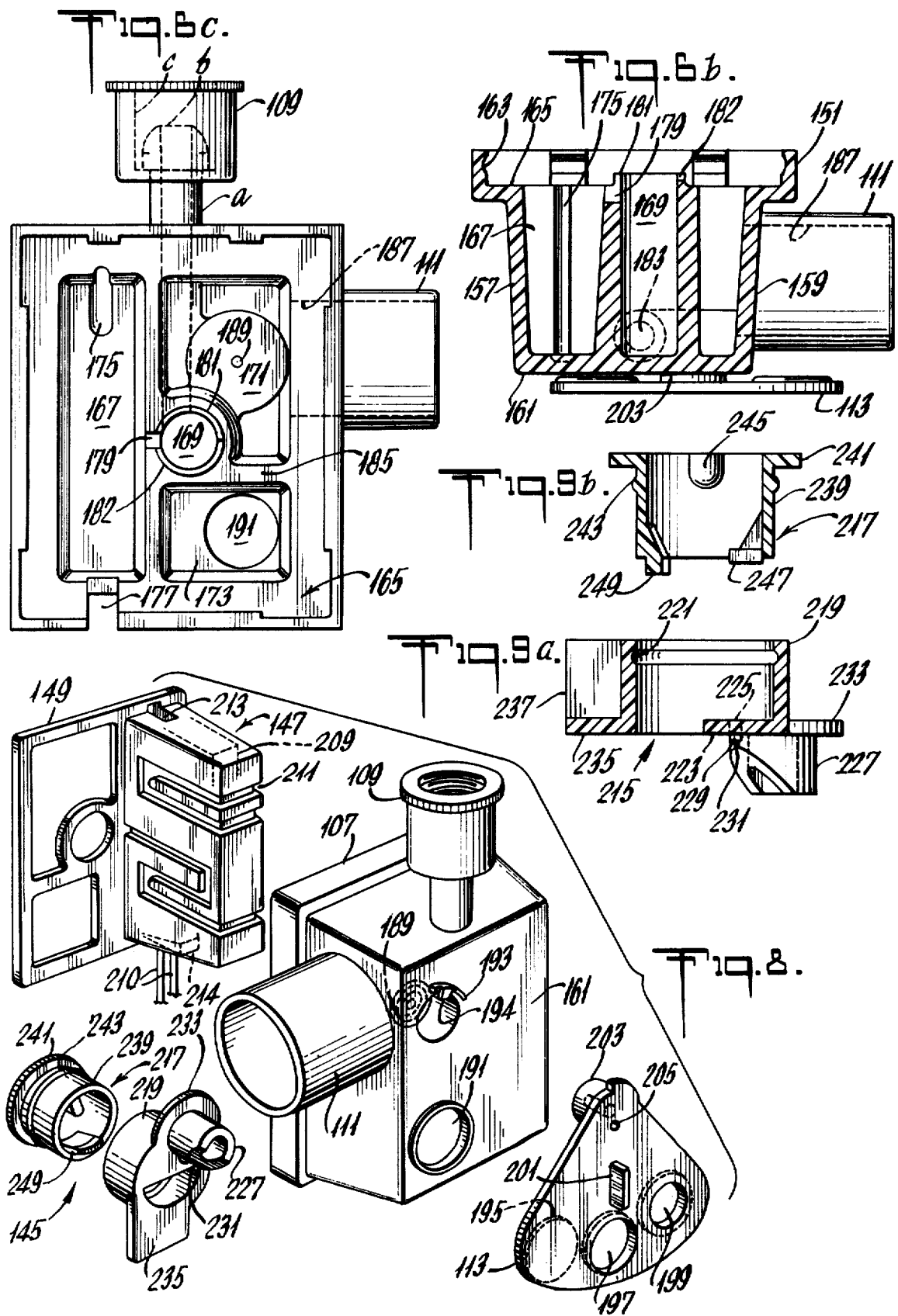

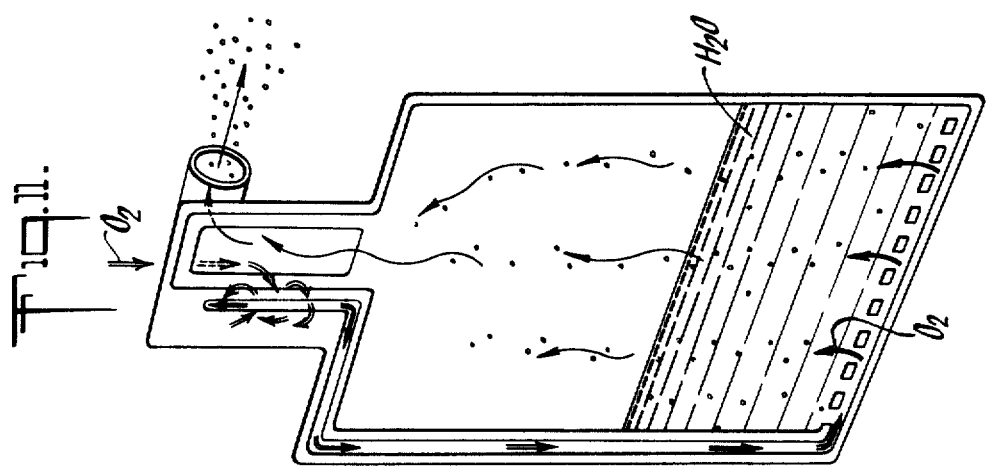
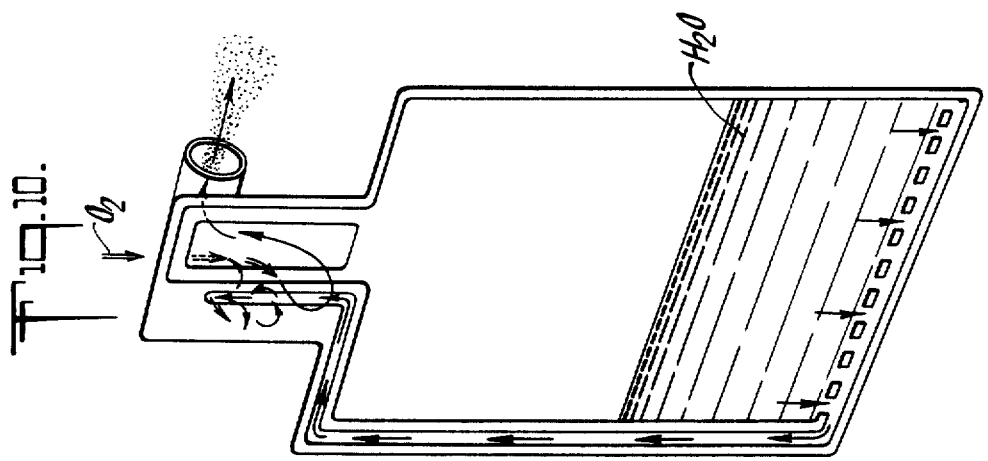

FLUID HEATING APPARATUS

BACKGROUND OF THE INVENTION

Most humidifiers presently on the market bubble the oxygen through water to pick up moisture. This is accomplished by passing the oxygen through a porous medium or screen which is located below the surface of the water. These so-called "bubblers" are limited in the amount of mass transfer they are able to achieve and will typically produce up to about 40% relative humidity (referred to body temperature) when operated at room temperature. An additional 10% may be achieved when a nebulizer is used as a humidifier. Both apparatuses depend upon the oxygen and water interfacing for a length of time and in such a manner that the contact is maximized. However during operation the operating temperature decreases and efficiencies therefore decrease.

An effective approach to increasing efficiency is to increase the molecular energy of the substances by heating. The addition of heat has been a standard scheme for increasing efficiency whereby the addition of small amounts of heat increase operating efficiencies to near saturation.

However, the nebulizer and humidifier units presently available in the art have many disadvantages and drawbacks. Many of them are quite expensive. Reusable units require special handling and sterilization.

Units with heaters have even more problems. Since these heaters have been either of the immersion type or the cuff type, they heat the entire water supply, thusly requiring a warm up time before operating efficiencies are reached and using large amounts of power. As a result they are quite inefficient. Moreover, these types of heating elements present a severe burn hazard. Most of them have high failure rates, require long down times for repairs and build up deposits which reduce operating efficiency quite markedly. Most units are quite bulky, taking up large inventory spaces.

What is desired therefore is an improved humidifier and an improved nebulizer, preferably a single unit with an interchangeable dual function. What is also desired are improved components for such a unit. An inexpensive and disposable nebulizer nozzle is needed. An inexpensive and efficient heating unit which is safe to handle and which heats only the water being used and when it is to be used instead of the entire water supply is also needed. A water container which is inexpensive and disposable and which is easily storable when not in use is needed. Safety features should be resident in the unit to protect the patient. Moreover the unit should be of a design which is easily and inexpensively manufactured and which is easily cleaned and repaired.

SUMMARY OF THE INVENTION

This invention is directed to an inflow heating uniting for use in a nebulizer to heat water in transit from a water reservoir to a nebulizer nozzle.

A housing may have a truncated pyramidal chamber and may provide the structure which may be connected between the nebulizer nozzle and water reservoir.

A heating unit which may be inserted into the housing chamber and is preferably shaped to mate with the chamber walls. This heating unit may include an electrical resistance heating element which may be coated with a biocompatible material such as silicone rubber. Preferably this coating is of sufficient thickness to provide for the formation of a relieved channel in the external surface of the heating unit of sufficient cross-sectional area needed for fluid flow. This coating should also possess compression properties which may provide a pressure fit for the mating with the housing.

Located in this coating may be the above-mentioned relieved channel which may interface with the chamber walls to form a water passgeway. This channel may meander over the surface of the coating in rectilinear maze fashion to provide an extended heat transfer area for the water in transit from the water reservoir to the nebulization nozzle.

A gasket may be formed as an end cap to the insert.

DESCRIPTION OF THE DRAWINGS

The advantages and unique features of this invention will best be understood from a reading of the following Detailed Description in conjunction with the accompanying drawings in which like numerals refer to like parts and in which:

FIG. 1 is a perspective view of the assembled nebulizer-humidifier.

FIG. 2 is a side elevation of this device.

FIGS. **3*a* and *b*** show the water bag in perspective and side elevation, respectively.

FIG. 4 shows a cross-section of the preferred water bag.

FIG. **4*a*** shows a perspective view of an alternate embodiment of the bag.

FIG. 5 is a sectional view of the bag boss.

FIG. **5*a*** is a sectional view of an alternate boss.

FIGS. **6*a*, *b*, and *c*** show a perspective view of the inside of the housing, a sectional view through the housing, and an elevation of the base of the housing, respectively.

FIG. 7 shows a perspective view of the outside of the housing.

FIG. 8 shows the housing and the heater insert and gasket, the combination orifice and insert, and the air valve which are assembled onto the housing.

FIGS. **9*a* and *b*** show sectional views of the venturi orifice component and the baffle-diverter component, respectively, of the combination orifice and valve insert.

FIG. 10 presents fluid flow paths for the apparatus as used as a nebulizer.

FIG. 11 presents fluid flow paths for the apparatus as used as a humidifier.

DETAILED DESCRIPTION OF THE INVENTION

The objectives of this invention are realized in a medical nebulizer-humidifier apparatus for use with oxygen breathing systems, wherein the apparatus may be manufactured in reusable and disposable models. The materials of which each model is constructed will determine whether a model will be reusable or disposble with the mechanical configuration being essentially alike for both models.

The subject nebulizer-humidifier unit may be used, mutually exclusively, in the nebulizer mode and in the humidifier mode. An adjustment is made while the components are being assembled to determine in which operational mode the apparatus is to operate. The operational purpose of the apparatus can be further interchanged, but a partial disassembly and reassembly of the components is required. As a nebulizer, the apparatus creates a water mist whereby the water particles produced are sized such that their mean diameters are in the 1–10 micron range. This molecular water vapor is delivered to the patient via the oxygen delivery apparatus. As a humidifier, air or oxygen is bubbled through the water supply to generate humid air which is fed to the patient.

A flexible plastic bag 101, FIG. 1, will hold an initially sterile water supply for the unit. This bag 101 may be refilled with water as needed. Located within the bag 101 is a passageway 103 which may be used to pass oxygen into the bag 101 or to draw water out of the bag 101. A hanging member 105 which can be a hook, loop, or the like, is used to support the bag 101 and the entire apparatus when disconnected from the oxygen supply.

A housing unit 107 connects to the bag 101. This housing unit 107 has an oxygen supply connector 109 and a mist duct 111. The housing 107 is mountable onto one side of the bag 101 as seen in FIG. 2. The housing 107 thusly extends outwardly from the other surface of one side 115 of the bag 101 with the oxygen connector 109 and the mist duct 111 extending upwardly and outwardly, respectively. In the operating mounted position the housing 107 and its attached bag 101 are supported by the oxygen supply connector 109.

An air mix valve 113 is positioned on the outer wall of the housing 107 away from the surface of the bag 101. This valve may be operated to mix room air with the generated mist to dilute the concentration of water vapor and oxygen delivered to the patient by fixed increments.

The features of the above recited components as well as the other components present in this apparatus will be discussed in detail below.

In the preferred embodiment, a flexible, collapsible plastic bag 101 is used as a water supply reservoir. This bag 101, FIGS. 3a, b, is constructed of two sheets of plastic material such as polypropylene or polyethylene heat sealed or otherwise bonded together at the edges. The size and shape of each plastic sheet comprising the bag 101 may be varied to provide various sized and shaped reservoirs. A first sheet, forming a first side 115 of the bag 101, FIG. 3a, is made from a flat sheet of 6 millimeters thick polypropylene material. A second sheet, forming the second side 117 of the bag 101, FIG. 3b, is also made from a sheet of 6 millimeters thick polypropylene material. This second side 117 is vacuum formed into a belled or puffed shape to provide a spacing between the walls of said first and second sides 115, 117 when the edges of these sides 115, 117 are heat sealed or otherwise joined together. Preferably each side 115, 117 has a larger portion 119 which is essentially rectangular and which when mated together cooperate to hold the entire water supply. Each of the sides 115, 117 could also have a smaller rectangular portion 121 which extends from its larger portion 119 creating an air space above the water level. Located at the free end of the smaller portion 121 of the bag 101 is the loop 105. This loop 105 functions as a support member for the bag 101 and is the mechanism by which the bag 101 may be hung from a support stand when not in use. The loop 105 is made as an integral part of the smaller portion 121 being formed by punching out a hole of rectangular, triangular or circular shape. Plastic reinforcement may be used around the loop 105. As suggested above, other thicknesses and other materials may also be used for one or more parts of this bag 101.

Located through the smaller portion 121 of the flat side 115, is a round hole 123 approximately 0.150 inches in diameter. Also located through the smaller portion 121 of this flat side 115, near the round hole 123 is a rectangularly shaped hole 125 of approximately 1 by 3 inches in size. These holes 123, 125 may be formed by punching-out the first sheet 115 before assembly. In the manufactured bag 101, these holes 123, 125 permit access to the interior of the bag 101.

Extending downwardly, in an assembled, hanging bag 101, from the round hole 123 to the bottom of the bag 101 is the passageway 103. This passageway 103 is formed by heat sealing a part of the belled side 117 to the flat side 115 of the bag 101. The passageway 103 has a semicircular cross section approximately 0.12 inches in diameter with a heat seal area of from 0.20 to 0.25 inches wide on either side. The path of this passageway 103 extends along an outer edge of the bag 101 to the bottom of the bag 101 and across the bottom. Located in the bottom section of passageway 103 are a plurality of evenly spaced slits 127. These passageway slits 127 are formed by dicontinuities in the passageway's inner heat seal and permit access between the passageway 103 and the water reservoir portion of the bag 101. The slits 127 may be formed permitting openings of approximately 0.04 inches. When the apparatus is in operation, the slits 127 provide a diffuser function. This passageway 103 may alternately be created by a channel formed in the flat side 115 which when mated with a corresponding flat portion of the belled side 117 thusly creates the passageway 103. Further the passageway 103 may also be created by the mating of the sides 115, 117, wherein both of the sides have channels which create the passageway 103 on mating. The cross-sectional shape of the passageway 103 may be varied as desired or as a result of the manner in which the passageway 103 is created.

Located about the round hole 123 and the rectangular hole 125 is a boss 129, FIG. 3a. This boss 129 is used to attach the housing 107 to the outer surface of the flat side 115 of the bag 101 and is shaped as a lazy block "nine" about the round and rectangular holes 123, 125. This boss 129 essentially forms a rail completely about the rectangular hole 125 and about the round hole 123 with the exception of a leg which if not absent would naturally bear upon the passageway 103 extending downwardly from the round hole 123. The exclusion of this leg gives the boss 129 the lazy "nine" configuration. The cross section of this boss 129, FIG. 5, is essentially rectangular with a protrusion extending outwardly in a plane parallel to the flat side at the outer surface of the boss 129. This protrusion may be rounded, triangular, semicircular, or simply tapered back to the boss wall. It is used as a pressure interlock with a mating portion of the housing 107. The boss 129 may be constructed by injection molding of polycarbonate, acetal, polypropylene or polyethylene or other plastic material, as durability and disposability requires, and has the bag 101 attached to it by heat sealing, adhesives or other means. This boss 129 configuration may be changed as needed to provide a mounting and sealing element between the bag 101 and the housing 107.

Being constructed of the relatively flexible and resilient materials described above, the boss 129 will give as a housing 107 is snapped onto and off of it. Thus, the resilient properties of the material allow for an interlocking pressure fit and release with the housing 107. In some instances, however, lesser mounting and release pressure is desired. In these instances the boss 129 is structured with a living hinge 134 at its outer surface, FIG. 5a. The living hinge 134 is formed by having the boss member overlap upon itself to the outside, so that the protruding portion is overlapped to the outside of the boss 129 configuration with this overlap pointing to that base of the boss 129 which meets the bag's 101 flat side 115. This alternate structuring reduces the amount of side pressure which the boss 129 can withstand and therefore makes and removal of the housing easier.

A removal tab 132 may be located on one side of the boss 129 or 130. This tab is connected to the base structure of the boss 129 or 130 by a living hinge 134. This tab is intended to be pivoted about the hinge attachment point on the boss 129 or 130 to be used as a lever to pry an interlocked housing 107 from the boss 129 or 130. The removal tab 132 is rectangularly shaped and of large enough dimensions to engage the edge of an interlocked housing 107 and to provide the mechanical advantage needed to overcome the locking pressure against the housing 107.

Where needed the bag 101 may have alternate configurations or other shapes some of which have special shapes designed to prevent kinking of the passageways. A second configuration 131 is shown in FIG. 4a. Here, there is a first flat side 133 and a second belled side 135 to the bag 131. However, in this embodiment there is only one essentially rectangular portion 131 which may have extremely rounded corners. The rectangular water reservoir portion of the bag 131 may have its sides pre-shaped or flared-in at the middle. This shape as shown in FIG. 4a, permits a redirection of the normal stress forces on the bag due to the weight of the water contained therein. With this flared edge shape, the forces are distributed radially in a uniform manner in such a way that the forces which would normally tend to compress or kink the passageways 103 and 139 are greatly reduced or completely eliminated.

A hanging flap or loop 137 extends from the end of the bag 131. This flap 137 contains a reinforced hole by which the flap 137 and thusly the bag 131 may be supported.

As in the preferred embodiment, a round hole 123 and a rectangular hole 125 exist in the upper portion of the flat side 133 of the bag 131. A passageway 139 is formed by heat sealing part of the belled side 135 to the flat side 133. This passageway 139 extends from the round hole 123 upwardly and then parts into two legs which travel along the edges of the bag 131 to its bottom. The bag 131 therefore has a dual leg passageway 139. Openings or slits 127 open the bottom leg of the passageway 139 to the interior or water reservoir portion of the bag 131. A boss 141 or like construction to the preferred boss 129 is heat or otherwise sealed about the holes 123, 125. This boss 141 is of reflected image configuration to the boss 129, i.e., the open leg looks upwardly instead of downwardly.

While two embodiments of this bag 101, 131 have been discussed above, other embodiments can exist without departing from the scope of the invention. For example, the first bag 101 could have a dual leg passageway 139 formed in it. Any bag could have the flared edge configuration. The size and shapes of the parts may be varied while still maintaining their functions. Moreover, the size and thickness of the materials used will vary as a function of the intended size and durability of the water reservoir. Typically the bag 101 is designed to hold up to 500 cubic centimeters of water and will have "500 cc", "250 cc", and "fill line" indications embossed on the sides. For a bag capable of holding this volume the overall dimensions of the bag may be 8 to 11 inches long by 5 to 6 inches wide with the belled side protruding about ¾ to 2 inches from its mating flat side.

Each embodiment of the bags 101, 131, FIGS. 3a, 4a. respectively, may have a pressure sensitive, adhesive coated or heat sealed rectangular cover patch 143 which protects the boss 129, 141 and the access holes 123, 125 and maintains the sterility of the inside of the bags 101, 131 before the apparatus is first assembled. This cover patch 143 is also useful for keeping the water from escaping from the bags 101, 131 when they are supplied prefilled with sterile water.

A housing 107, FIG. 6a, holds other components comprising the nebulizer-humidifier. Included among the components is a combination venturi orifice and valve insert 145, a water heater insert 147 and a gasket 149. The housing structure is injection molded of polycarbonate, acetal, polypropylene or polyethylene depending upon its intended length of use. The more durable materials are used for more permanent models.

In the preferred embodiment, housing 107, FIGS. 6a, b, c, are injection molded of polycarbonate plastic in an essentially truncated pyramidal shape. The housing walls are mounted upon a rectangular base 151, FIG. 6a, which steps out from the walls and then turns at a right angle to extend away from the end of the housing walls. With the housing 107 attached to the bag 101, the housing 107 presents top 153, bottom 155 and side 157, 159 walls and an outer side 161. The walls of the base 151 have intermittent protuding surfaces 162 located in the inner base 151 walls. At each protrusion 162 is located a concave undercut 163. Each of these undercuts 163 extend into the base 151 inner face to form a cavity approximately 0.030 inches deep and 0.145 inches wide. These undercuts 163 engage the boss 129 protrusions to hold the bag 101 onto the housing 107. The stepout of the base 151 from the walls 153, 155, 157, 159 of the housing provides a shoulder or seating surface 165 at the jointure of the base 151 and walls 153, 155, 157, 159. A spacing of about .19 inches exists between the undercut 163 and the seating 165.

The housing 107 has four chambers 167, 169, 171 and 173. The first chamber 167 is of truncated narrow pyramidal shape and extends into the housing from the base to the outer side 161. This chamber 167 is located next to the first side wall 157 so as to communicate with the round hole 123 in the bag 101 when said bag 101 is mounted to the housing 107. A channel 175 may run longitudinally down the center of the top 153 inner wall and continues partially down the center of the outer side 161 inner wall of this chamber 167.

A rectangular section of the base 151 and bottom 155 wall of the housing is cut out along the cross section centerline of the chamber 167. This cutout 177 extends to about mid-depth of the chamber and is approximately equal in width to the bag passageway 103 leading from the round hole 123.

The second chamber 169 adjoins the first chamber 167 and is cylindrically shaped to extend into the housing 107 from base seat 165 plane to the outer side 167. This chamber 169 extends parallel to the first chamber 167 at about the nominal center of the housing 107. With the housing 107 secured to the boss 129, this second chamber 169 communicates with the bag's rectangular hole 125.

Located through the wall adjoining the first 167 and second 169 chambers is square transfer portal 179 being about 0.05 inches on a side. This portal extends parallel to the base seating 165 plane and connects a centerline of the first chamber 167 with a centerline of the second chamber 169.

Extending partially about the opening to the second chamber 169 and outwardly from the plane of the base seat 165 is a first venturi spacer 181. This spacer 181 is a curved plate which extends from the transfer portal 179 in a clockwise arc of about 180° when looking at the base seat 165.

Also extending partially about the second chamber 169 opening is a second venturi spacer 182. This second spacer 182 is a curved plate which extends from the end of the first spacer 181 in a clockwise arc of about 120° when looking at the base seat 165. This second spacer 182 does not extend as far above the base seating plane 165 as does the first spacer 181. As will be further discussed, the difference in the heights of the two venturi spacers 181, 182 provides the venturi chamber spacing in the venturi nozzle of the assembled housing 107.

The oxygen supply connector 109 protruding from the top wall 153 of the housing 107, includes an extension tube 109a, with a pressure fit head 109b and a locking nut 109c. The head 109b and lock nut 109c are sized to receive a standard sized pressure line from an oxygen supply flow meter. The extension tube 109b is provided passageway into the pressure end of the second chamber 169, the end nearest the outer side 161, by a circular oxygen portal 183 extending through the housing top wall 153 and the outer side 161.

The third chamber 171, FIG. 6b, extends parallel to the first two chambers 167, 169, from the base seat 165 plane to the outer side 161 of the housing 107. This chamber borders the top wall 153 and second side wall 159 and has a relieved rectangular cross section with the relief being provided by the instrusion of the walls of the second chamber 169 into a corner of the rectangle. The breadth of this rectangle is defined by the distance between the walls of the first chamber 167 and the second side wall 159. The length of this rectangle is defined by the distance from the top wall 153 of the housing to an inner partition wall 185. This partition wall 185 extends parallel to the housing top wall 153 and tangentially to the second chamber 169, from that part of the second chamber's 169 wall away from the housing top wall 153 to the housing second side wall 159. With the housing 107 positioned on the bag boss 129 this chamber 171 communicates with the bag rectangular hole 125.

Tubular mist duct 111 exhausts this third chamber 171 through the second side wall 159 by connecting to a circular mist exhaust port 187 through the wall 159.

A pressure relief valve structure 189 extends into the housing's outer side 161 at the back of this third chamber 171. This relief valve structure 189 is of standard design. Included is a rubber gasket 190 which seats in the bottom of the relief valve cavity 189 to provide the pressure release mechanism. An insert positionable into the relief valve cavity 189 against the gasket will be discussed below during the discussion of the air mix valve 113.

The fourth chamber 173 adjoins each of the other chambers 167, 169, 171, is essentially rectangularly shaped, and extends parallel to the other chambers 167, 169, 171. This chamber is defined by the meeting of the partition wall 185, the second side 159, and bottom 155 walls, the outer side 161 and the adjoining first chamber 167 wall. Extending through the rear of this chamber, i.e through the outer side 161, is an air mix portal 191. This portal has a tapered, flanged mouth at the outer side 161 of the housing 107.

Situated partially about the pressure relief valve structure 189 on the outer side 161 of the housing 107 is a curved limit plate 193, FIG. 7. This plate transcribes an angle of approximately 80° and is used to limit the rotational operation of the air mix valve 113. Protruding from the inner curvature of this limit plate 193, in the center portion of the curve is a tab 194. This tab 194 extends outwardly from the top of the limit plate 193 in a plane parallel to housing outer wall 161. The purpose of this tab 194 is to interfere with a portion of the air mix valve 113 when the valve has been rotated into position to keep the air mix valve 113 from pulling out of the housing 107.

Air mix valve 113, FIGS. 7, 8, includes a flat, pie-sectional plate having three circular protrusions 195, 197, 199 on the underside of the valve 113, each being spaced along its outer arc. A thumb plate 201 protrudes outwardly from the center of the valve's 113 top side. Extending from the underside of the valve 113 at the acute angle of piesection is the pressure relief valve insert 203. This insert 203 mates with the valve structure 189 in the housing's outer side 161 to seat against the gasket 190. A flange extends partially about this insert 203. Because of the circular configuration, the relief valve permits pivoting of air mix valve 113 to locate one of the protrusions over the air mix portal 191. The first protrusion 195 is a circular disk and closes off the air mix portal 191 when positioned over it. The second protrusion 197 has an included circular opening which permits an opening and access to a portion of the air mix portal 191 when this protrusion 197 is positioned over the air mix portal 191. The third protrusion 199 has an included circular opening which permits lesser opening and access of a lesser portion of the air mix portal 191 when this protrusion 199 is positioned over it. Located at the relief valve insert 203 area of the plate is a small through hole 205. Escaping air passing through this hole 205 creates a whistling sound when the relief valve operates. With the air mix valve protrusions 195, 197 or 199 in position at the air mix portal 191 the interfering tab 194 is mated with the insert 203 flange to secure the air mix valve 113 to the housing 107.

A tubing adapter 207, is insertable into the mist duct 111 for connecting to a range of from 0.110 inches to 0.402 inches diameter tubing.

Insertable into the first chamber 167, in a pressure fit, is the heater unit 147, FIG. 8. This unit is a resistance wire wound heater element 209 as manufactured by Watlow Inc. having thermostatic control for operation between 90° F. and 110° F. The heater element 209 is rectilinearly shaped and is fiberglass reinforced and encapsulated to proper dimensions for use. The element 209 is encapsulated in biocompatible insulation such as silicone rubber to form a truncated narrow pyramidal outer shape. Molded into the outer surface of the silicone rubber is a tortuous canal 211 which transverses first one long side of the pyramid and then the other and then back again in rectilinear maze fashion. An initial layer or coating insulates the heater while a second thickness or layer defines the edges or bounds of the canal 211 by the absence thereof.

Formed as a continuous part of the heater's 147 silicone jacket is a gasket 149. The gasket 149 is essentially rectangular in shape and provides an end cap to the insert 147, establishing a seal thereby, being formed to sit upon the housing's base seating surface 165 when the heater 147 is inserted into the first chamber 167. The gasket 149 is approximately 0.10 inches thick and contains cutouts or openings for the second, third, and fourth chambers 169, 171, 173, respectively, and for the first chamber channel 175. This latter opening 212 to channel 175 includes a small rectangular hole 212 connecting to a small rectangular furrow 213 in the surface of the heater 145 which mates with the first chamber's top wall 153.

In an alternate embodiment, the gasket 149 may have, instead of the rectangular hole 212 and furrow 213 into the heater 149 structure, a circular hole 216 mating to a circular passageway 218 which extends through the heater 149 silicone rubber coating to a section of the tortuous canal 211. In this embodiment the first chamber channel 175 is not necessary and therefore eliminated.

The electric power supply wires 210 to the heater element 209 extend through the side of the heater 145, which is opposite the side containing the furrow 213. These wires pass through a built-up rectilinear shoulder 214 which acts to protrude through the housing cut out 177 to seal this area when the heater 145 and gasket 149 are fully inserted into the housing 107.

The combination venturi, orifice and valve insert 145, FIGS. 9a and 9b, is insertable into the second chamber 169 to cooperate with this chamber 169, the venturi spacers 181, 182, the square transfer portal 179 and the gasket 149 to form venturi nozzle structure. This insert 145 has a venturi orifice component 215 and a baffle-diverter component 217 which snaps into the orifice component 215.

The orifice component 215 has a reference cylinder 219 which has a semicircular annular groove 221 about its inside wall a short distance from one end, hereby designated the open end of the cylinder. The other end of the cylinder is one-half closed by a semicircular cap 223. Located through this end cap 223 is a circular hole or aerosol orifice 225. Extending perpendicularly from the outside of the cap 223 so as to transect the aerosol orifice 225 is a dowel-shaped plug 227. The outer surface of this plug 227 interrupts approximately one-half of the aerosol orifice 225. Cut into the surface of the plug 225, extending outwardly from the aerosol orifice is, a semicircular venturi chamber excavation 229. This excavation 229 is an extension of the aerosol orifice 225 and opens a space which is an extension of the dimensions of the cross section of the aerosol orifice 225. The length of this excavation is equal to the venturi spacing of the nozzle which in turn is equal to the height of the step in the venturi spacing shoulders 181, 182; that is the difference between the heights of the venturi spacers 181, 182. Extending along the remaining surface of the plug 227 is a nozzle channel 231 which may be semicircular. This plug channel 231 connects to the venturi excavation 229 and is in alignment with the excavation 229 and aerosol orifice 225. Thus, from an end view, the aerosol orifice 225, venturi excavation 229 and nozzle channel 231 are concentrically aligned.

The cross-sectional are of the nozzle channel 231 is as needed to define the jet orifice of a venturi nozzle. The length or excursion of the venturi excavation 229 is as needed to define the venturi chamber spacing of a venturi nozzle. Likewise, the dimensions of the aerosol orifice 225 are as needed to define the venturi nozzle's aerosol orifice.

The free end of the plug may be hollowed and truncated to save materials and reduce the friction surface of the jet orifice, respectively.

The cylinder partial cap 223 also includes a semicircular extension or skirt 233 about the venturi chamber excavation 229 end, of the plug 227. This skirt 233 cooperates with the cylinder partial cap 223 to provide a circular bearing surface upon which the plug 227 may be rotated when inserted in the second chamber 169 of the housing 107 to seat upon the venturi first spacer 181 and to compress the gasket 149 creating a seal around the outside perimeter of the first and second venturi spacers 181, 182.

A rectangular-like baffle 235 having an arc portion missing, as defined by an arc portion of the reference cylinder 219, extends outwardly from the cylinder 219 in the plane of the partial end cap 223. This baffle is positioned at the open half side of the cylinder 219 and extends normally to the edge of the partial cap 223 which cuts the diameter of the cylinder 219 cross section. The midpoint of the baffle 235 cuts the cylinder 219 at a point diametrically across from the aerosol orifice 225.

A support strut 237 attached to the cylinder 219 outer wall surface, supports the baffle 235 along a centerline.

The baffle-diverter insert 217, has a cylindrical portion 239 and a knurled ring extension 241 at one end thereof. This knurled ring extension 241 permits the baffle-diverter insert 217 to be rotated when positioned within the reference cylinder 219 of the venturi orifice component 215. Extending outwardly about the cylindrical portion 239 outer wall is an annular ring 243. This ring 243 is at a location to interlock with the reference cylinder 219 annular groove 221 when the baffle component 217 is fully inserted into the orifice component 215.

A round bead 245 is suspended on the inner wall and at the knurled ring 241 end of the insert cylinder 239. This bead is alignable with the aerosol orifice 225 and is used as an impact surface for the created mist.

A diverter bar 247 extends normally to the inner wall surface of the insert cylinder 239 at the opposite end from the bead 245. This diverter bar 247 is situated 90° about the cylindrical from the bead 245.

A limit stop plate 249 extends beyond the diverter bar 247 end of the insert cylinder 239 and around the inside wall of this cylinder 239 for an arc of 90°. The nozzle-valve insert 145 is assembled by having the baffle-diverter component 217 inserted into the orifice component 215 so that the limit plate 249 protrudes beyond the cylinder partial end cap 223. The limit plate 249 is positioned so as to establish the diverter bar 247 over the aerosol orifice 225 at one stop, and to position the bead 245 in alignment with the aerosol orifice 225 at the other stop. A stop is established when an end of the limit plate 249 butts against the cylinder cap 223. The diverter bar 247 rides upon the cylinder cap 223 inside surface as the diverter component 217 rotates within the nozzle component.

A housing 107 unit is assembled by inserting a heater insert 147 into the first chamber 167 with the accompanying gasket 149 sitting upon the seating surface 165. The pressure relief gasket 190 is positioned in the relief structure 189. The air mix valve 113 is attached to the housing by the pressure relief valve insert 203 being inserted into the relief structure 189. The orifice and valve insert 145 is assembled as discussed above. This insert 145 is then operated to position the diverter bar 247 over the aerosol orifice 225 for humidifier operation or to align the bead 245 with the aerosol orifice for nebulizer operation.

With the insert 145 seated into the housing 107, the gasket 149 opening about the second chamber 169, the venturi spacer 181, the outer wall surface of the plug 223 and the cap extension 233 cooperate to form a passageway from the square transfer portal 179 to the venturi chamber excavation 229.

The insertion of the plug 227 portion of the insert 145 into the second housing chamber 169 with the nozzle component baffle 235 covering the largest portion of the fourth chamber 173 opening after the gasket 149 is installed, completes the assembly of the housing 107.

The housing 107 may then be snapped onto the bag boss 129, with the oxygen connector 109 extending upwardly. Thusly, the entire apparatus is assembled and is ready for connection to outside apparatus. Power lines to the heater element 209 are connected to a 110-120 volt, 60 HZ supply. The oxygen connector 109 may be connected to a permanent or a portable oxygen supply. These supplies, such as those at a hospital wall outlet, are pressurized to 50 pounds per square inch. In most instances therefore, a flow meter regulator is used to interface the oxygen supply and the housing connector 109. This flow meter is of the standard type which can regulate the pressure output from 2 psi to 50 psi, for a volume of oxygen from 1 to 15 liters per minute. In the nebulizer mode it is desirable to have the oxygen supply pressure as seen by the nebulizer connector 109 between 6 and 10 psi with a volume of 4 to 12 liters per minute. In the humidifier mode it is desirable to have the oxygen supply as seen by the connector between 2 and 6 psi with a volume of 1 to 8 liters per minute. Mist duct 111 may be connected to a face mask, a nasal canulae, a face tent or other patient breathing apparatus.

The nebulizer bag 101 is intended to hang vertically when in operation. When operated in the nebulizer mode, FIG. 10, water is fed to the nozzle from the water reservoir in the bag 101 via the passageway slits 127, the passageway 103, the tortudus heater can 211 where it is heated, the square transfer portal 179, the passageway formed by the meeting of the wall of the nozzle plug 227, the venturi spacers 181, 182, the gasket 149, the base seating surface 165, and the venturi chamber formed by the plug excavation 229. Oxygen is fed to the nozzle via the oxygen supply connector 109 and the second chamber 169. The oxygen is forced through the nozzle's jet orifice which was created by the mating of the wall of the second chamber 169 and the nozzle channel 231 residing on the nozzle plug 227. The gas expands as it passes out of the orifices and into the venturi chamber to draw off droplets of water present in the chamber. The mixture is then forced through the larger aerosol orifice 225 and is impinged upon the bead 245 to further reduce water particle size. The mixture then passes through a lower portion of the rectangular bag hole 125 and into the bag 101 above the water level. The velocity of the mixture is suddenly reduced and the larger particles of water drop out of suspension. The oxygen with what is essentially 1-10 micron sized water molecules then passes through the upper portion of the rectangular hole 125 into the third housing chamber 171 and out of the housing 107 via the mist duct 111. A slight vacuum created in the fourth housing 173 by the flow of gases permits the dilution of the mixture with room air when the air mix valve 113 is operated to open the air mix portal 191. The pressure relief valve associated with the third or exhaust chamber 171 protects the patient from excessive pressures, and creates an audible alarm if the tubing to the patient becomes kinked, depriving the patient of the humidifier oxygen.

When operated in the humidifier mode, FIG. 11, the oxygen which enters the housing 107 via the connector 109 and the chamber 169 is diverted in the nozzle area by the position of the diverter bar 247 over the aerosol orifice 225. The oxygen therefore passes from the venturi chamber excavation 229, through the passageway created by the venturi spacer 181, the gasket 145, and other components as discussed above, through the heater canal 211, through the round bag hole 123, and through the bag passageway 103 to the passageway slits 127. The stream of oxygen is diffused through these openings 127 to bubble up through the water held in the bag 101. Moist air collects at the top of the bag 101 and exits via the rectangular bag hole 125, the housing third chamber 171 and the mist port 111.

A versatile and economical nebulizer-humidifier has therefore been created. Due to their design the water reservoir and nebulization nozzle may be manufactured cheaply enough to be disposable after a specific medical use. The remaining components are easily dismantled for cleaning and autoclaving. The water reservoir bag 101 is also refillable and is easily stored as empty or as filled with sterile water. The heater insert may be used with or without a heater element.

Many changes can be made in the above-described apparatus and many different embodiments of this invention could be made without departing from the scope thereof, it is intended that all matter contained in the above description or shown in the accompanying drawings, therefore, shall be interpreted as illustrative and not in the limiting sense.

What is claimed:

1. In combination with a medical device including a nebulizer having a venturi-type nozzle and a fluid supply, a fluid heating apparatus, comprising:

a housing having a chamber provided therein, said chamber having a truncated pyramidal shape and having access openings through the walls thereof connected to said fluid supply and connected to said nozzle; a truncated pyramidal shaped insert positioned in said housing and having situated therewithin a heating element having electrical leads thereto, said heating element including a rectilinearly shaped, wound resistance wire heater element, and a rubber coating material surrounding said heater element, the outer surface of said coating material providing a truncated pyramidal shape and including a relieved channel in the outer surface thereof, said channel traversing said insert surface in rectilinear maze fashion, and forming a passageway from said fluid supply opening to said nozzle opening at the interfacing surfaces of said chamber walls and said insert when said insert is inserted into said chamber in a pressure fit.

* * * * *

UNITED STATES PATENT AND TRADEMARK OFFICE
CERTIFICATE OF CORRECTION

PATENT NO. : 4,084,587
DATED : April 18, 1978
INVENTOR(S) : Joseph W. Lindsey

It is certified that error appears in the above-identified patent and that said Letters Patent are hereby corrected as shown below:

At Column 3, Line 19, "other" should be -- outer --.
At Column 4, Line 20, "dicontinuities" should be -- discontinuities --.
At Column 5, Line 8, after "makes" and before "and," insert -- mounting --.
At Column 5, Line 51, "141 or" should be -- 141 of --.
At Column 8, Line 22, "angle of piesection" should be -- angle of pie section --.
At Column 9, Line 62, "cross-sectional are" should be -- cross-sectional area --.
At Column 11, Line 41, "heater can 211" should be -- heater canal 211 --.
At Column 11, Line 52, "of the orifices" should be -- of the jet orifices --.

Signed and Sealed this

First Day of May 1979

[SEAL]

Attest:

RUTH C. MASON
Attesting Officer

DONALD W. BANNER
Commissioner of Patents and Trademarks